(12) United States Patent
Yan et al.

(10) Patent No.: US 10,603,211 B2
(45) Date of Patent: Mar. 31, 2020

(54) PHACOEMULSIFICATION NEEDLE WITH IMPROVED SAFETY AND MANUFACTURABILITY

(71) Applicant: INNOLCON MEDICAL TECHNOLOGY (SUZHOU) CO. LTD, Suzhou (CN)

(72) Inventors: Zhongyu Yan, Suzhou (CN); Wei Luo, Suzhou (CN)

(73) Assignee: INNOLCON MEDICAL TECHNOLOGY (SUZHOU) CO. LTD, Suzhou (CN)

( * ) Notice: Subject to any disclaimer, the term of this patent is extended or adjusted under 35 U.S.C. 154(b) by 205 days.

(21) Appl. No.: 15/318,921

(22) PCT Filed: Apr. 25, 2015

(86) PCT No.: PCT/CN2015/077469
§ 371 (c)(1),
(2) Date: Mar. 7, 2017

(87) PCT Pub. No.: WO2016/000482
PCT Pub. Date: Jan. 7, 2016

(65) Prior Publication Data
US 2017/0189232 A1 Jul. 6, 2017

(30) Foreign Application Priority Data
Jul. 2, 2014 (CN) .......................... 2014 1 0309064

(51) Int. Cl.
*A61F 9/007* (2006.01)
*A61L 31/04* (2006.01)
(Continued)

(52) U.S. Cl.
CPC ........ *A61F 9/00745* (2013.01); *A61L 31/022* (2013.01); *A61L 31/04* (2013.01); *A61M 39/10* (2013.01); *A61M 2039/1033* (2013.01)

(58) Field of Classification Search
CPC .............. A61F 9/00745; A61F 9/00736; A61F 2250/0093; A61F 9/007; A61M 39/10; A61M 3/0279; A61B 2017/320084
(Continued)

(56) References Cited

U.S. PATENT DOCUMENTS 5,651,783 A 7/1997 Reynard
5,667,489 A * 9/1997 Kraff .................. A61F 9/00745
604/22
(Continued)

FOREIGN PATENT DOCUMENTS

CN 102256574 A 11/2011
CN 104055620 A 9/2014
(Continued)

*Primary Examiner* — Eric J Rosen
*Assistant Examiner* — Andrew P. Restaino
(74) *Attorney, Agent, or Firm* — Seed Intelectual Property Law Group LLP

(57) ABSTRACT

An ultrasonic phacoemulsification needle with improved safety and manufacturability, comprising: a metal connection body and a plastic needle in a splitting structure. The plastic needle is connected at the distal end of the metal connection body, and the metal connection body is connected to the distal end of an ultrasonic hand piece. The ultrasonic phacoemulsification needle employing a design of splitting the connection body and the needle alleviates the difficulties for manufacturing otherwise caused by the conventional phaco tip designs. It reduces the surgical costs from patients. In addition, the ultrasonic phacoemulsification needle using a plastic body reduces the likeliness of punctuating the capsule bag, which otherwise easily occurs (Continued)

in the metal needle case due to the extremely sharp rigid tip at the end of the needle, thus the risks of surgery are reduced and safety is improved.

16 Claims, 3 Drawing Sheets

(51) Int. Cl.
*A61L 31/02* (2006.01)
*A61M 39/10* (2006.01)

(58) Field of Classification Search
USPC .......................................... 606/107
See application file for complete search history.

(56) References Cited

U.S. PATENT DOCUMENTS

| | | | | |
|---|---|---|---|---|
| 5,746,713 | A * | 5/1998 | Hood | A61F 9/00745 |
| | | | | 604/22 |
| 5,935,096 | A * | 8/1999 | Barrett | A61F 9/00745 |
| | | | | 604/22 |
| 5,989,208 | A | 11/1999 | Nita | |
| 6,270,471 | B1 | 8/2001 | Hechel et al. | |
| 8,439,938 | B2 | 5/2013 | Moore, Jr. | |
| 2010/0160852 | A1 | 6/2010 | Moore, Jr. | |
| 2012/0221009 | A1 * | 8/2012 | Tada | A61B 17/7258 |
| | | | | 606/93 |
| 2012/0316490 | A1 * | 12/2012 | Perkins | A61F 9/00745 |
| | | | | 604/22 |
| 2014/0074011 | A1 | 3/2014 | Charles | |
| 2014/0074013 | A1 | 3/2014 | McCary et al. | |
| 2015/0196426 | A1 | 7/2015 | Kuebler et al. | |

FOREIGN PATENT DOCUMENTS

| | | |
|---|---|---|
| CN | 104055622 A | 9/2014 |
| CN | 203988621 U | 12/2014 |
| CN | 204072457 U | 1/2015 |
| CN | 204072458 U | 1/2015 |
| CN | 204734603 U | 11/2015 |
| CN | 105310821 A | 2/2016 |
| EP | 2712591 A1 | 4/2014 |
| WO | 2014/048550 A1 | 4/2014 |

* cited by examiner

PHACOEMULSIFICATION NEEDLE WITH IMPROVED SAFETY AND MANUFACTURABILITY

BACKGROUND

Technical Field

The present invention relates to ultrasonic needles, which are medical devices, and more particularly relates to the field of ultrasonic surgery, ophthalmologic surgery, phacoemulsification and vitrectomy.

Description of the Related Art

In the past two decades, ultrasonic surgeries are widely applied in various cases. Both for the types of surgeries and for the number of patients, they have increased significantly, especially in the field of cataract surgery, due to its unique advantages, the ultrasonic emulsification technique has been widely adopted by the majority of ophthalmic surgeons and patients of all ages.

Cataract is a common eye disease that can cause blindness if not treated. Within a human eye, there is one part called the lens. Under normal circumstances, the lens is transparent; light beams pass through it and the other related refractive tissues, and then reach the retina, so one can clearly see the external objects. For some reasons, once a lens becomes opaque, it will affect the image formed on the retina, so one cannot see things clearly anymore. The lens opacity leads to vision loss, and this opacified lens is defined as cataract.

There are three major types of cataract surgery: intracapsular cataract extraction surgery (ICCE), extracapsular cataract extraction surgery (ECCE), and phacoemulsification (Phaco). Compared with the traditional large incision cataract surgery by which the cataract was extracted as a whole body, phacoemulsification (Phaco) is a minimally invasive surgery. With this phaco surgery, an about 2-3 mm incision is made along the edge of the cornea. Through this small incision, an ultrasonic needle is inserted into the eye to break the cloudy lens and other tissues. With an aspiration/irrigation system, the broken tissues are sucked out, while the anterior chamber pressure is maintained, then an IOL is implanted, so that patients is able to see again.

For a phacoemulsification (Phaco) surgical system, it typically includes below major components: Ultrasonic electric generator, irrigation/aspiration mechanism, phacoemulsification hand piece and phacoemulsification needle (or called tip). In the phaco hand piece is an electric to acoustic converter, which converts the ultrasonic frequency electrical signals into ultrasonic mechanical vibrations. The principle of phacoemulsification cataract removal is described as this: a power ultrasonic transducer in the hand piece converts the electrical energy into mechanical energy of the high-speed small amplitude vibration, the ultrasonic vibration amplitude is amplified by a mechanical transformer in the distal end of the hand piece, then through the connected phacoemulsification needle such ultrasonic vibration is applied to the human tissue to cause crushing, cutting, emulsification, and to improve on aspirating the tissue outside the body, and then with the intraocular lens implantation, the patient's vision is restored. Compared with the traditional intracapsular, extracapsular cataract surgeries, a small incision phacoemulsification causes fewer complications and quicker recovery of vision. This treatment can also be used to remove cataracts before they mature, so an early treatment is made possible.

In most cases, phacoemulsification needles are machined from titanium alloy or other metal materials, and the needle connecting section used to connect onto the distal end of the hand piece is designed with the needle itself, i.e., the proximal end of the phaco needle is made as a connecting mechanism, such as threads. This design of one body needle makes the ratio of the aspiration hole length and diameter so great that it is difficult to make and costly. This type of single use needle has added financial considerations to doctors and patients who want to use this surgical technology, especially for the developing countries. Thus it potentially hinders the ultrasonic technology being fully used to the patients in developing countries in emerging markets. On the other hand, with titanium alloy or other metal materials made phaco needle, its distal tip is sharp and rigid, make it easy to pierce the capsular bag, increase the risk of surgery.

BRIEF SUMMARY

The present invention provides a safe and economical phacoemulsification needles to resolve the difficulty of making existing phacoemulsification needle, to reduce the machining costs, and then the overall surgical costs. The existing metal phaco needles have sharp rigid tip, it can easily pierce the capsule bag, increase the risk of surgery, while the plastic needle shall alleviate this issue. In general, the present invention with this two body design of ultrasonic tools also applies to making other ultrasonic surgical instruments.

A phacoemulsification needle with improved safety and manufacturability, comprising: a metal connector and a plastic needle, the metal connector and the plastic needle body are sub-structures; the plastic needle is connected to the metal connector body; the metal connector is attached to the distal end of a phacoemulsification hand piece.

Preferably, the metal connector is made with a bore along the axis running through the center of the connector body. The shape of the said bore matches with the said plastic needle body shape for receiving the said plastic needle. The center axis of the said central bore coincides with the central axis of the said connector body.

Preferably, the metal connector comprises threaded section for connecting to a phacoemulsification hand piece threaded portion and a tapered section for fixing the plastic needle body. The said threaded section has threads made on the outer surface of connector body, and the said tapered section is located at the proximal end of the threaded section, which is adapted to the receiving bore shape of the hand piece.

Preferably, the tapered portion is cut along the center axis two mutually perpendicular slits. At distal end of the threaded section is provided with a fastening portion. The said fastening portion has surfaces for wrench gripping; it has adapted shape and size to a corresponding wrench.

Preferably, the plastic needle is a tube with uniform diameter and its distal end is wedge-shaped. Alternatively, the plastic needle is a tube with uniform diameter and its distal end curved wedge-shaped. Alternatively, the plastic needle is a stepped tube with its proximal end diameter is greater than the distal diameter.

The beneficial effects of the present invention are presented as improved safety and manufacturability. The split sub-structure design of a phacoemulsification needle with a connector body and needle body reduces the design effort and the difficulty of manufacturing. The lowered cost then brings down the expense from patents. At the same time, due to the use of medical grade plastic material for the phacoemulsification needles, it avoids the sharp rigid tip, which can easily pierce the capsular bag. Thus, the risk of the surgery is reduced and the safety of the surgery improved.

DETAILED DESCRIPTION

With reference to the illustrating embodiments shown in the figures, the present invention is described in detail in the following paragraphs. But the present invention is not limited to these embodiments. Based on these embodiments and the descriptions, alternative structures, methods, or the functions made by ordinary skills in the art are included within the scope of the present invention.

The words used to describe herein the position and orientation within the invention are based on the hand piece operator as a reference, The end near the operator is named the proximal end, and away from the operator the distal end.

Figure 1:
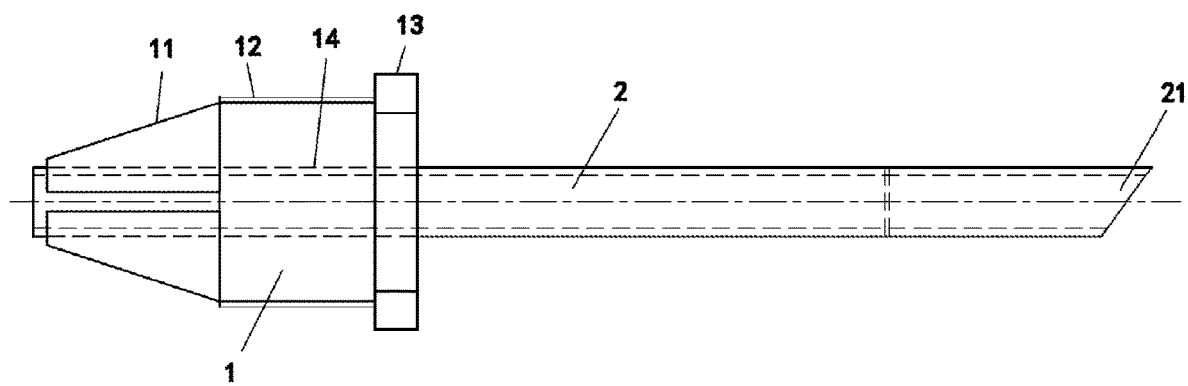
FIG. 1 is a schematic view of the invention. It illustrates the structure of the first embodiment
Figure 2:
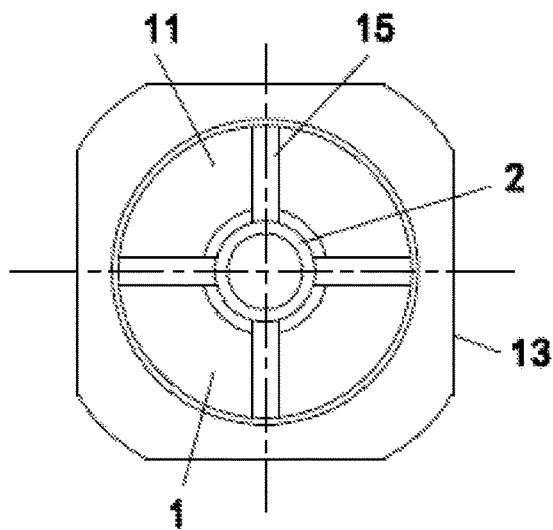
FIG. 2 is a left side view of FIG. 1.

Referring to FIGS. 1 and 2, a structural diagram of the first embodiment of the present invention of phacoemulsification needle, it includes metal connector 1 and plastic needle 2. The metal connector 1 and the plastic needle 2 are two sub-structures. The plastic needle body 2 is connected to the metal connector 1. The connector 1 is attached to the distal end of the phacoemulsification hand piece.

The following describes a first embodiment of the invention: the metal connector 1 uses medical grade metallic material; the plastic needle body 2 made of medical grade plastic material. The metal connector body 1 is provided along the axis a central bore 14 running through the body 1. The central bore 14 having a needle with the plastic body 2 adapted to the shape, size of the central bore 14 is slightly larger than the size of the plastic needle body 2, for receiving the plastic needle body 2. The central axis of the central bore 14 coincides with the central axis of the metal connecting body 1.

Figure 5A:
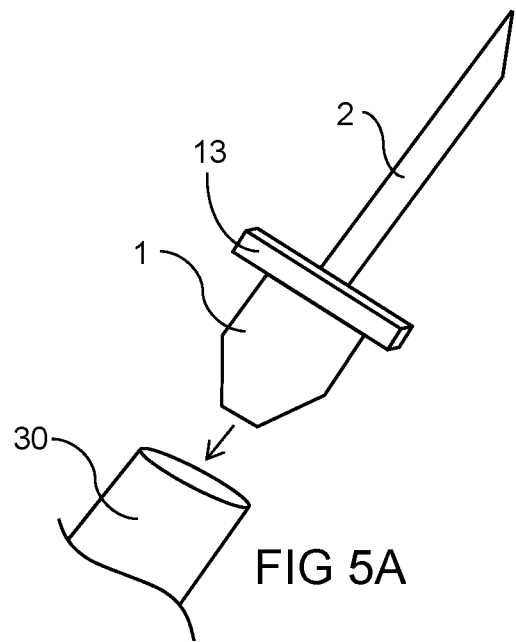
FIG. 5A is an exploded diagram of the phacoemulsification needle prior to being coupled to an ultrasonic hand piece.
Figure 5B:
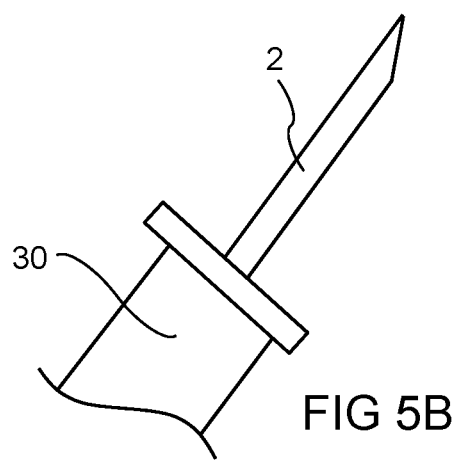
FIG. 5B is a diagram of the phacoemulsification needle coupled to an ultrasonic hand piece.

The connector 1 comprises a threaded portion 12 for connecting to the ultrasonic phaco hand piece 30 and a tapered portion 11 for fixing the plastic needle body 2. The said thread portion 12 is the threaded area positioned on the outside of the distal end of the connector 1. The said tapered portion 11 is positioned at the proximal end of the threaded portion 12, and the said tapered portion 11 is made to match the inner lumen shape at the distal end of the phaco hand piece 30, see for example FIGS. 5A and 5B. On the said tapered portion 11 are two mutually perpendicular slits 15. At the distal end of the threaded portion 12 is fastening feature 13. The said fastening feature 13 is surfaces for wrench tools, with matched shape and sizes.

When applying the first embodiment of the invention of phacoemulsification needles, the threaded portion 12 on the metal connector 1 engages the internal threads at the distal end of phaco hand piece 30, i.e., the metal connector 1 is screwed into the distal end of the hand piece; the tapered portion 11 fits with the hand piece internal conical surface. Under this condition, the slit 15 is partially closed in the process of screwing and squeezing into the lumen, that the tapered face of the tapered portion 11 is closely attached to the inner wall of the hand piece. Due to the deformation of the slit 15, the diameter of the central bore 14 will shrink. Thus, the plastic needle body 2 was rigidly coupled to the metal connector 1, and then coupled to the distal end of the hand piece 30. So the ultrasonic vibration can be very effectively transmitted to the surgical tool tip. For the first embodiment, the plastic needle tube 2 diameter is uniform shape, its distal end 21 is of wedge-shaped structure.

Figure 3:
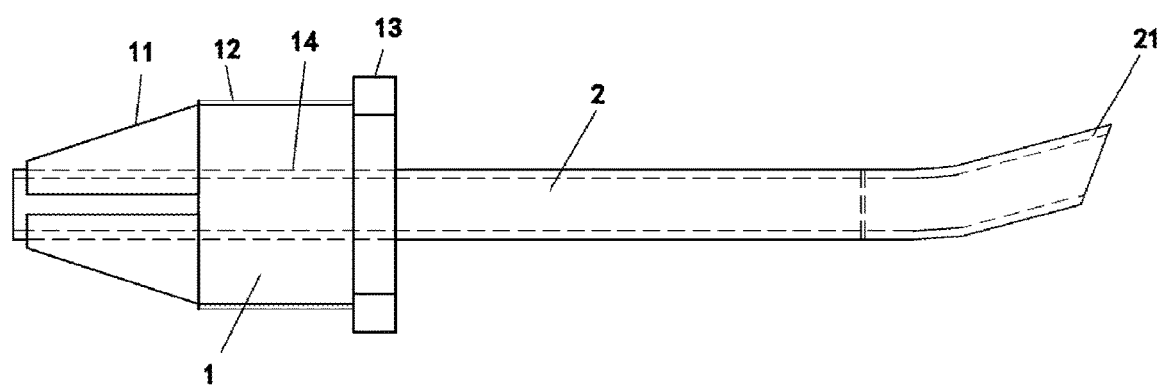
FIG. 3 is a schematic diagram of the invention. It illustrates the structure of the second embodiment

With reference to FIG. 3 of the second embodiment of the phacoemulsification needle, which differs from the first embodiment, the said plastic needle body 2 is a uniform diameter tube, but its distal end 21 has a curved section of the tip of the wedge-shaped structure. The curved section of the present embodiment can improve the visibility and easiness of operation. In the tiny surgical site, particularly in surgical microscope required case, the curved tool tip allows a doctor to see more easily and also easy to reach the difficult access surgical field, such as the corner, deep area. Further, the tip having a curved section is also increased ultrasonic cavitation effects.

Figure 4:
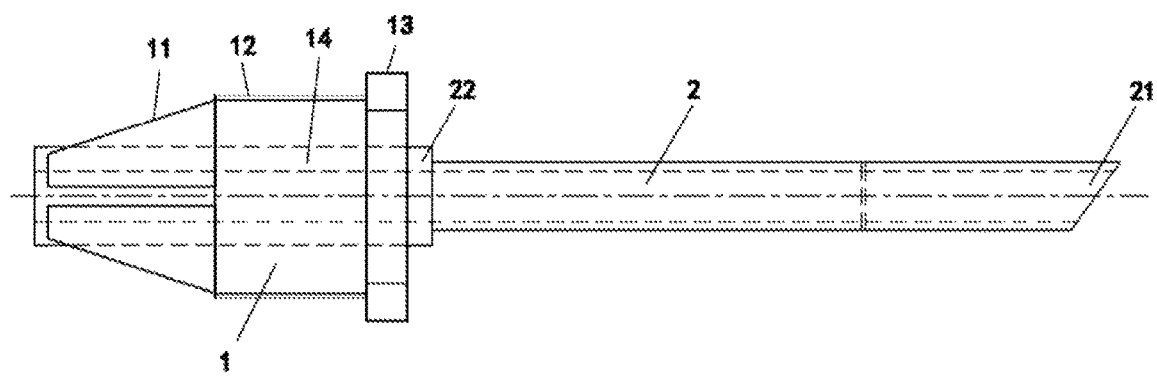
FIG. 4 is a schematic diagram of the invention. It illustrates the structure of the third embodiment

With reference to FIG. 4 of the third embodiment of the phacoemulsification needle, differs from the first embodiment and the second embodiment, the said plastic needle body 2 is stepped tube shape, the diameter of the proximal end 22 is greater than the diameter of the distal end 21. The reason: the proximal end 22 of the needle body 2 generally has higher stress due to ultrasonic vibration; increasing the diameter of the proximal end 22 helps to reduce this stress, thus reduces the risk of needle breakage. Since the needle body is made of plastic, it can more easily achieve this structure, but for the metal needles of the prior art, it is difficult to achieve and high cost.

The present invention, since the connector body 1 is made of rigid metal material, it can be a good fit secured with the phaco handpiece. Plastic needle 2 is made of medical grade plastic resin material; plastic needle 2 length needs to be designed within a certain range so not to attenuate much of ultrasonic vibration.

Since the metal connector 1 with a plastic needle body 2 using split design of two bodies, it reduces the difficulty of the design and manufacturing. Meanwhile, the use of medical grade plastic needle body 2 avoids the sharp rigid pointing distal tip that can easily pierce the capsular bag. The present invention overcomes the limitation in the prior art that connection to the ultrasonic hand piece can only take metal emulsification needle. It also solves the technical problems in the prior art that metal emulsifying needle is difficult to make, the tip is too rigid and sharp, so it has good market prospects.

It should be understood that although the present specifications are described according to the embodiment, but not every embodiment contains only an independent technical solution, such as: plastic needle body 2 of the invention in addition to the preferred embodiment of the invention, made of a medical resin, a metal material may also be used for making the needle body, but with the metal connector body it is a split sub-structure. For the first and second embodiments of the present invention, the proximal end of the plastic needle body 2 can also use ladder-shaped tube design. Also, the present invention of the third embodiment, the distal end of the plastic needle body 2 ban make as a curved wedge-shaped structure 21. This narrative description is merely for clarity, those skilled in the art will appreciate that the specification as a whole, the embodiments of the technical solution can be suitably combined to form other embodiments, the skilled person can understand.

A series of detailed description set forth above are merely a specific explanation for the feasibility embodiment of the present invention, they are not intended to limit the scope of the present invention. The equivalent skill who have not traveled out of the spirit of the present invention made equivalent embodiments or change should be included within the scope of the present invention.

The invention claimed is:

1. A phacoemulsification needle comprising:
  a metal connector body including a connecting portion at a distal end and a tapered portion at a proximal end; and
  a plastic needle body having a first portion and a second portion, wherein:
    the metal connector body and the plastic needle body are two sub-structure bodies;
    the first portion of the plastic needle body is connected to the metal connector body;
    the second portion of the plastic needle body extends from the metal connector body at the distal end;
    the tapered portion of the metal connector body is configured to be received by a lumen of a distal end of a phacoemulsification hand piece;
    the connecting portion of the metal connector body is between the tapered portion and the second portion of the plastic needle body; and
    an outer surface of the connecting portion of the metal connector body includes threads configured to couple to threads of the phacoemulsification hand piece.

2. The phacoemulsification needle according to claim 1, wherein:
  the metal connector body has a central axis and a central bore that extends along the central axis;
  the central bore is configured to receive the first portion of the plastic needle body; and
  a center axis of the central bore coincides with the central axis of the metal connector body.

3. The phacoemulsification needle according to claim 1, wherein the tapered portion fixes the first portion of the plastic needle body to the metal connector body.

4. The phacoemulsification needle according to claim 3, wherein:
  the tapered portion includes two cuts that are perpendicular to each other;
  the connecting portion has a fastening portion; and
  the fastening portion has a wrench tool gripping surface having shape and size adapted to a wrench tool.

5. The phacoemulsification needle according to claim 1, wherein the plastic needle body is of uniform diameter tube shape and the second portion has a distal end that is a wedge-shaped structure.

6. The phacoemulsification needle according to claim 1, wherein the plastic needle body is of uniform diameter tube shape and the second portion has a distal end having a curved section with a wedge-shaped structure.

7. The phacoemulsification needle according to claim 1, wherein the plastic needle body is a stepped tube shape, wherein the first portion has a first diameter that is greater than a second diameter of the second portion.

8. The phacoemulsification needle according to claim 1, wherein the first portion of the plastic needle body is connected to an inner surface of the metal connector body at the proximal end.

9. A phacoemulsification needle comprising:
  a metal connector body having a connecting portion at a distal end and a tapered portion at a proximal end, the metal connector body having a bore; and
  a plastic needle body having a proximal end received in the bore of the metal connector body and a distal end extending away from the bore at the distal end of the metal connector body,
  wherein the connecting portion of the metal connector body is connected to a phacoemulsification hand piece and the tapered portion is received by the phacoemulsification hand piece.

10. The phacoemulsification needle according to claim 8, wherein the bore is a central bore, wherein the connecting portion includes threads for connecting to the phacoemulsification hand piece,
  wherein the threads are on an outer surface of the distal end of the metal connector body;
  wherein the tapered portion is disposed at the proximal end of the metal connector body;
  wherein the tapered portion is adapted to be coupled to an inner lumen of a distal end of the phacoemulsification hand piece; and
  wherein the tapered portion includes two mutually perpendicular slits so that the tapered portion has a deformation margin to couple to the plastic needle body.

11. The phacoemulsification needle according to claim 10, wherein a distal end of the threaded portion is provided with a fastening portion that has gripping surfaces adapted to a wrench tool.

12. The phacoemulsification needle according to claim 9, wherein the metal connector body includes a tapered portion that is configured to be received by a lumen of a distal end of the phacoemulsification hand piece.

13. The phacoemulsification needle according to claim 12, wherein the metal connector body includes outer threads that couple the phacoemulsification needle to the distal end of the phacoemulsification hand piece.

14. The phacoemulsification needle according to claim 9, wherein an outer surface of the connecting portion of the metal connector body includes threads configured to couple to threads of the phacoemulsification hand piece.

15. The phacoemulsification needle according to claim 9, wherein the connecting portion of the metal connector body is located between the tapered portion and the distal end of the plastic needle body.

16. A phacoemulsification needle comprising:
  a metal connector body including a connecting portion at a distal end and a tapered portion at a proximal end, wherein an outer surface of the connecting portion includes threads configured to connect the phacoemulsification needle to a distal end of a phacoemulsification hand piece; and
  a plastic needle body having a first portion and a second portion, wherein:
    the metal connector body and the plastic needle body are two sub-structure bodies;
    the first portion of the plastic needle body is connected to the metal connector body;
    the second portion of the plastic needle body extends from the metal connector body at the distal end; and the tapered portion of the metal connector body is configured to be received by a lumen of the distal end of the phacoemulsification hand piece.

* * * * *